(12) United States Patent
Dinse et al.

(10) Patent No.: US 10,492,740 B2
(45) Date of Patent: Dec. 3, 2019

(54) DEVICE AND METHOD FOR A DIAGNOSTIC DEVICE

(71) Applicant: SIEMENS HEALTHCARE GMBH, Erlangen (DE)

(72) Inventors: Franziska Dinse, Heiligenstadt (DE); Michael Fuhrmann, Herzogenaurach (DE); Philip Hafner, Zirndorf (DE); Michael Hufnagel, Nuremberg (DE); Joerg Krauss, Bayreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 254 days.

(21) Appl. No.: 15/526,030

(22) PCT Filed: Sep. 16, 2015

(86) PCT No.: PCT/EP2015/071162
§ 371 (c)(1),
(2) Date: May 11, 2017

(87) PCT Pub. No.: WO2016/074829
PCT Pub. Date: May 19, 2016

(65) Prior Publication Data
US 2017/0311907 A1  Nov. 2, 2017

(30) Foreign Application Priority Data
Nov. 11, 2014 (DE) .......................... 10 2014 222 935

(51) Int. Cl.
*A61B 6/06* (2006.01)
*A61B 6/08* (2006.01)
(Continued)

(52) U.S. Cl.
CPC .................. *A61B 6/06* (2013.01); *A61B 6/08* (2013.01); *A61B 6/4452* (2013.01);
(Continued)

(58) Field of Classification Search
CPC .. A61B 6/461; A61B 6/06; A61B 6/08; A61B 6/4452; A61B 6/4458;
(Continued)

(56) References Cited

U.S. PATENT DOCUMENTS 6,999,551 B2   2/2006   Bressel et al.
7,500,783 B2   3/2009   Kalender
(Continued)

FOREIGN PATENT DOCUMENTS

DE        10222397 A1    4/2003
DE     102006044783 A1   4/2008
(Continued)

*Primary Examiner* — Chih-Cheng Kao
(74) *Attorney, Agent, or Firm* — Laurence Greenberg; Werner Stemer; Ralph Locher

(57) ABSTRACT

A device and to an associated method for a diagnostic apparatus. A housing unit can be aligned by way of a securing unit which is connected to the housing and it can be controlled in such a way that the diaphragm unit which is connected to the x-ray source and is arranged in the housing unit can be aligned in accordance with a specified position.

8 Claims, 2 Drawing Sheets

(51) Int. Cl.
*A61B 6/00* (2006.01)
*G21K 1/04* (2006.01)
(52) U.S. Cl.
CPC .......... *A61B 6/4458* (2013.01); *A61B 6/4464* (2013.01); *A61B 6/4476* (2013.01); *A61B 6/461* (2013.01); *A61B 6/469* (2013.01); *A61B 6/54* (2013.01); *A61B 6/542* (2013.01); *A61B 6/545* (2013.01); *G21K 1/04* (2013.01)
(58) Field of Classification Search
CPC ..... A61B 6/4464; A61B 6/4476; A61B 6/469; A61B 6/54; A61B 6/542; A61B 6/545; G21K 1/04
See application file for complete search history.

(56) References Cited

U.S. PATENT DOCUMENTS

| | | | |
|---|---|---|---|
| 9,161,728 | B2 | 10/2015 | Watanabe et al. |
| 2005/0152499 | A1* | 7/2005 | Zhao .................. G21K 1/04 378/147 |
| 2008/0130835 | A1* | 6/2008 | Peterson .............. A61B 6/4464 378/117 |
| 2014/0328456 | A1* | 11/2014 | Lee ...................... A61B 6/4452 378/28 |
| 2015/0117601 | A1* | 4/2015 | Keeve .................. A61B 6/589 378/41 |

FOREIGN PATENT DOCUMENTS

| | | |
|---|---|---|
| DE | 102012008812 A1 | 10/2013 |
| JP | 2013244190 A | 12/2013 |

\* cited by examiner

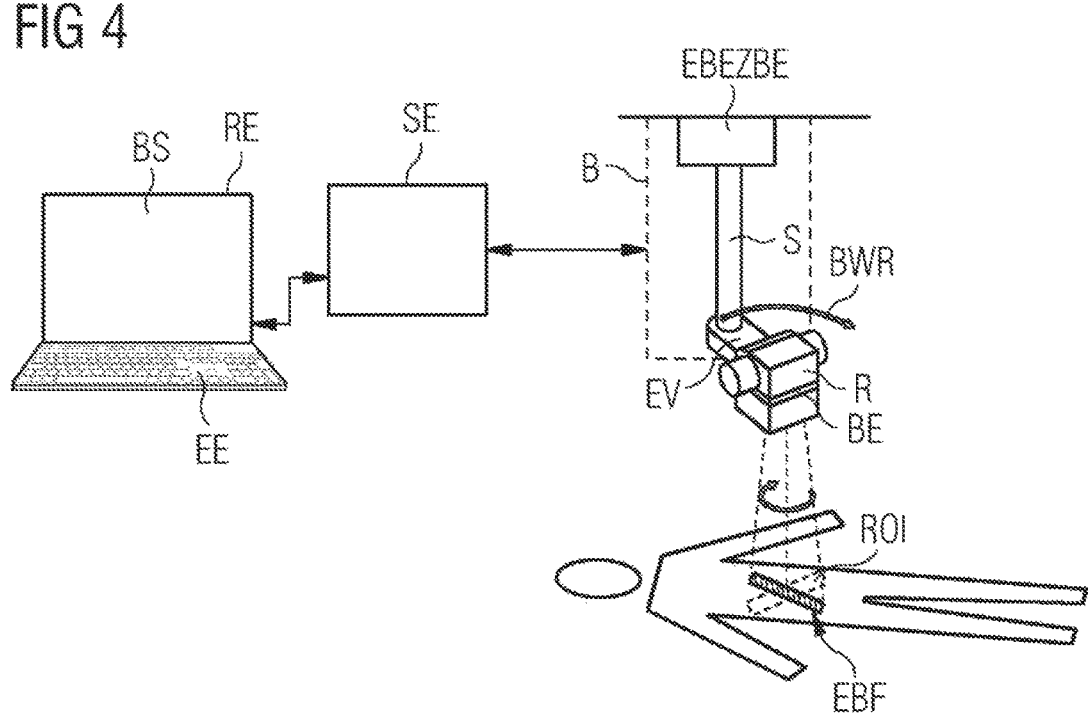
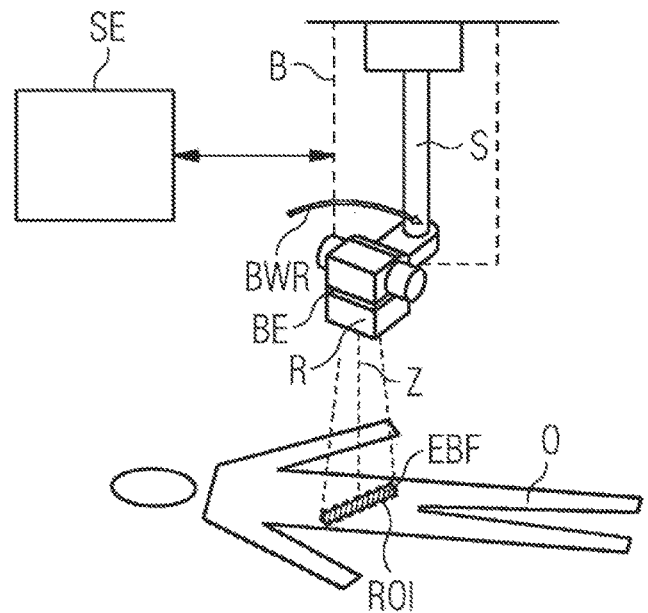

DEVICE AND METHOD FOR A DIAGNOSTIC DEVICE

BACKGROUND OF THE INVENTION

Field of the Invention

Medical devices with characteristics, for example, for radiography, fluoroscopy and angiography are used for diagnosis and treatment. In order to keep the X-ray burden on the patient as low as possible in each case, an X-ray window is set to the region to be examined, which can be designated the Region of Interest. The delimitation of the X-ray window can take place by means of a collimator unit equipped with collimator plates. The positions of the collimator plates of the collimator unit and, in particular, a rotation of the entire collimator unit can be carried out manually or by means of controllable electric motors which are arranged on the plates of the collimators and/or directly on the collimator unit. However, this arrangement and, in particular, the rotation of the entire collimator unit at the output of the X-ray head has the disadvantage that the housing enclosing the X-ray head and the entire collimator unit for the X-ray source to be used occupies a large volume. A further disadvantage lies in the restricted handling of the large housing. Apart from the disadvantage of a restricted positioning possibility, the housing of the X-ray source with a movable collimator unit has the further disadvantage that the mechanical system for the mounting and control of the X-ray source must be dimensioned larger.

It is an object of the invention to provide a further design of a housing of an X-ray unit provided with an X-ray source and a collimator unit.

SUMMARY OF THE INVENTION

This object is achieved by the features given in the claims.

This device and the associated method has a housing unit arranged on a positionable fastening unit with an X-ray source and a collimator unit arranged downstream of the X-ray source, wherein a control unit is provided and, for orientation of the collimator unit, the positionable fastening unit is controlled by it such that the collimator unit is orientable according to a specification.

Apart from the advantage that the collimator unit as well as the housing accommodating the X-ray source can be dimensioned small, that is, space-saving, the subject matter of the invention has the further advantage that in addition to the greater freedom of movement of the housing with the X-ray source and the collimator unit, a simpler orientation to an X-ray detector corresponding thereto is enabled.

The subject matter of the invention has the advantage that due to the weight reduction in the configuration of the collimator unit, the mechanism for the movement of the housing with the X-ray source and the collimator unit can be dimensioned more slender.

BRIEF DESCRIPTION OF THE SEVERAL VIEWS OF THE DRAWING

The subject matter of the invention has the advantage that the housing of the X-ray source is configurable compact. The subject matter of the invention will now be described by reference to schematic drawings. In the drawings:

FIG. 4 shows a part of a diagnostic device for generating an X-ray radiograph, and FIG. 5 shows a further view of the diagnostic device of FIG. 4.

DESCRIPTION OF THE INVENTION

In this device and the associated method, a housing unit is orientable by means of a controllable fastening unit connected thereto such that the collimator unit arranged in the housing unit and connected to the X-ray source is orientable according to a position specification.

Figure 1:
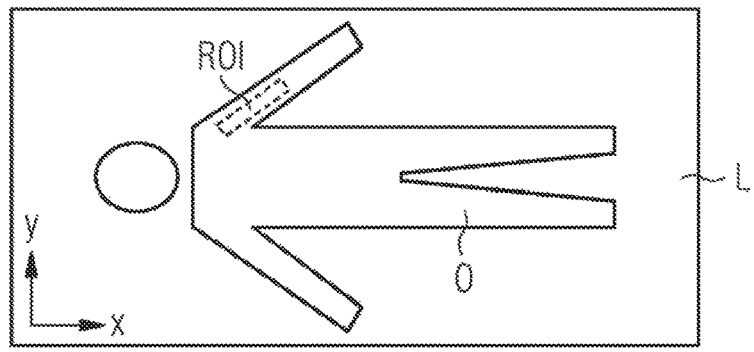
FIG. 1 shows a patient with a region to be investigated in a patient.

FIG. 1 shows schematically a patient O placed on a table L wherein, for example, an X-ray radiograph is to be made in the region of the upper arm. This region in the upper arm of the patient is marked as a region of interest ROI.

Figure 2:
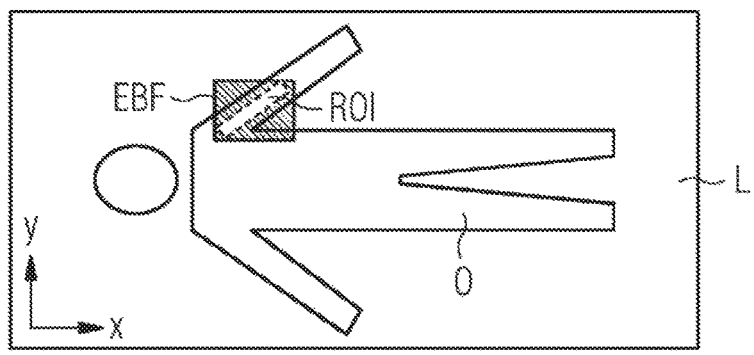
FIG. 2 shows the size of a possible X-ray radiograph.

In FIG. 2, the patient O placed on the table L is shown with the marked region of interest ROI and a possible X-ray field, which can also be designated the collimation field EBF. It can be seen that a much larger area in the region of the upper arm of the patient O would be irradiated with X-rays.

Figure 3:
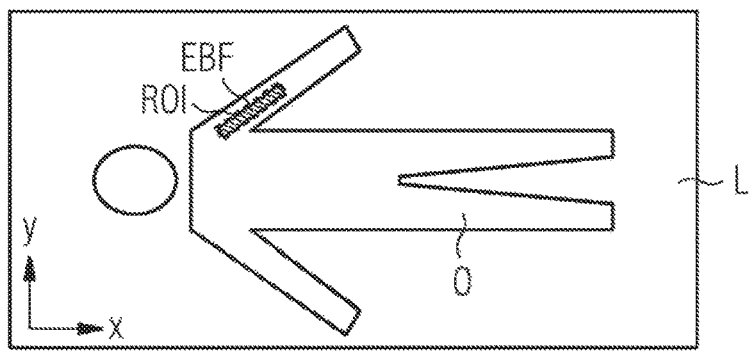
FIG. 3 shows a size of an X-ray image adapted to the examination region.
Figure 3:
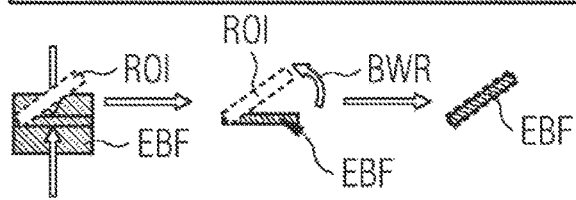

In FIG. 3, the X-ray field or collimation field EBF is accordingly adapted to a region to be investigated, which is also designated the region of interest ROI. In this figure, the sequence for acquiring the region of interest ROI by means of a targeted collimator setting is indicated. The X-ray field EBF is reduced according to the size of the region of interest ROI by means of suitable collimator plates. The collimator plates are each arranged in the collimator unit BE. A positioning of the collimator plates, for example, in their x and/or y-direction, can be carried out manually or by means of very small, space-saving electric motors. The collimation field EBF restricted to the region of interest ROI must be oriented, in a further step, according to the orientation of the region of interest ROI. Either the restricting collimation field EBF is rotated, for example, about one edge by this anticlockwise manually, semimanually or electronically until a match is achieved between the collimation field EBF and the region of interest ROI. A further procedure would be that the collimation field EBF is displaced, for example, in the y-direction until the center of the collimation field EBF coincides with the center of the region of interest ROI. Thereafter, there follows a rotation of the collimation field EBF clockwise or anticlockwise. The rotation of the collimation field EBF takes place by means of a rotation of the whole housing in which the X-ray source and the collimator unit is arranged. The movement of the collimator plates for adjustment of the collimation field EBF to the region of interest ROI can take place manually, semi-manually or electronically. A rotation of the collimator unit takes place through operation/control of the mechanism provided for the orientation of the X-ray source and the electric motors controlling it. For the orientation of the X-ray source, a computer unit with a control unit provided therefor but not explicitly described here is used. Through an input unit connected to the computer unit, by means of a screen, an orientation procedure can be visualized and the control unit integrated into the computer unit can initialize control signals for the setting of collimator plates and a rotation of the X-ray source with the collimator unit BE and carry them out in a controlled manner.

In FIG. 4, the diagnostic device and a region of interest ROI arranged within the patient are shown. A detector unit to be arranged under the patient O is not shown explicitly.

The part of the ceiling-mounted diagnostic device shown here is an X-ray source R accommodated in a housing and a collimator unit BE placed at the output of the X-ray source R with adjustable collimator plates. The X-ray source R and the collimator unit BE can be rigidly connected to one another. A rigid connection between the X-ray source and the collimator unit BE could also be unlocked and a rotation of the collimator unit could take place with the aid of a flange. The housing of the X-ray source R is movably arranged with a fastening unit B, for example, a multi-jointed arm in the ceiling region. In this schematic representation, the fastening unit B has firstly a movable first and second movement unit EBE, ZBE with which a positioning of the fastening unit B can be caused in the x-and/or y-direction. A height-variable stand is hung from the first and/or second movement unit EBE, ZBE. Arranged between the stand S and the housing of the X-ray source R is a pivotable first connecting unit EV. With this pivotable first connecting unit EV, inter alia for example, a displacement of the housing of the X-ray source R can be compensated for by means of the first and/or second movement unit EBE, ZBE in that a central beam Z of the X-ray source R directed toward a point in the region of interest ROI remains oriented there or, for example, can be rotated about a point in the region of interest ROI. In FIG. 4, the region of interest ROI is indicated on the patient. Additionally, the collimation field EBF already adapted to the width of the region of interest is shown. Also shown is the central beam Z emerging from the X-ray source R (see also FIG. 5). An overlap of the collimation field EBF with the region of interest ROI takes place with a matched control of the first and/or second movement unit EBE ZBE with the first connecting unit EV. The matched control results in a movement direction BWR of the housing of the X-ray source with the collimator unit B while maintaining the orientation of the central beam Z of the X-ray source R. The movement of the housing of the X-ray source R with the collimator unit BE can take place with movement support. By means of a light window which the collimation field EBF reproduces, the operator can move the housing with the X-ray source and the collimator unit BE in the movement direction BWR as shown so that the collimation field EBF overlaps with the region of interest ROI. For this purpose, the fastening unit B to which the housing of the X-ray source R with the collimator unit BE is fastened can be controlled either manually, semimanually or fully electronically such that the collimation field EBF coincides with the region of interest ROI. By means of the first connecting unit EV, the housing of the X-ray source R can be pivoted with the collimator unit BE about an axis extending in the center of the stand S. By means of the control unit SE, input of desired position data regarding the region of interest ROI and the size of the collimation field EBF can then be input. For this purpose, the control unit SE generates, for the first and second movement unit EBE, ZBE and for the first connecting unit EV, necessary control data concerning the orientation of the X-ray source R with collimator unit BE accommodated by the housing. The orientation can take place in such a way that a central beam Z of the X-ray source R remains in its orientation toward the region of interest ROI. The collimator unit BE thus rotates about the central beam Z. By means of the computer unit RE indicated, via an input unit EE and a diagnostic device shown on the screen BS, the momentary positioning of the housing accommodating, inter alia, the X-ray source and the collimator unit can be indicated and the orientation of the housing can be simulated or carried out step-by-step. According to the specification and orientation and the size of the region of interest ROI that is to be set, the control signals necessary for the fastening unit B and the first connecting unit EV as well as control signals necessary for the setting can be generated in the control unit SE and an exact positioning of the collimation field EBF to be oriented to the region of interest ROI can be carried out.

In FIG. 5, the diagnostic device represented schematically in FIG. 4 is shown in its end position. Following orientation of the collimation field EBF of the X-ray source R to the region of interest ROI, for example, an X-ray radiograph can be made. Not the collimator unit DE itself or, for example, a joint between the X-ray tube R and the collimator unit BE, but the components of the fastening unit B carry out the individual steps for the rotation movement and orientation of the collimation field EBF. The components of the fastening unit B move such that the collimator unit BE is oriented according to the specification of a region of interest ROI. This has the advantage that control means, in particular electric motors for carrying out a displacement and/or rotation of the entire housing unit in which, inter alia, the X-ray source R and the collimator unit BE are arranged are implemented. This also has the further advantage that the housing accommodating the X-ray source R and the collimator unit BE can advantageously be made smaller so that the rotation or positioning or orientation of the collimator unit BE can take place by means of parts of the fastening unit B. In a further embodiment of the invention, the orientation of the collimator unit BE can take place via a window control or via gestures that are analyzed by means of a camera by the operator of the diagnostic device and are converted into control signals.

LIST OF REFERENCE CHARACTERS

R X-ray source
BE Collimator unit
B Fastening unit
EBE First movement unit
ZBE Second movement unit
EV First connecting unit
S Stand
BWR Movement direction
Z Central beam
EBF Collimation field, X-ray field
ROI Region of interest
O Object
L Table
SE Control unit
EE Input unit
BS Screen
RE Computer unit

The invention claimed is:
1. A device, comprising:
a positionable fastening unit;
a housing unit disposed on said positionable fastening unit and including an X-ray source and a collimator unit arranged downstream of said X-ray source;
said collimator unit including displaceable collimator plates for delimiting a collimation field of said collimator unit;
a control unit for orienting said collimator unit together with said X-ray source, said control unit being configured to control said positionable fastening unit for rotating said collimator unit about a central beam of said X-ray source for aligning the collimation field with an examination region of interest.

2. The device according to claim 1, wherein, for orienting said collimator unit, said control unit controls said positionable fastening unit such that while maintaining an orientation of the central beam of said X-ray source, according to a position and orientation of the examination region of interest, a collimation field orientable thereto is rotated by way of said positionable fastening unit to thereby achieve a match between the examination region of interest and the collimation field.

3. The device according to claim 1, wherein said positionable fastening unit is formed of at least a first and a second movement unit mounted to a ceiling of a room and capable of travel in a plane.

4. The device according to claim 3, wherein said positionable fastening unit is a multi-jointed arm.

5. The device according to claim 3, which comprises a post of variable length mounted to said first or second movement units and having a free end, and a first connecting unit disposed on said free end, said first connecting unit being configured at least with one degree of freedom and having a connection to said housing unit with said X-ray source and said collimator unit arranged therein.

6. The device according to claim 1, wherein said X-ray source and said collimator unit are fixed relative to one another.

7. An x-ray adjustment method, comprising:
providing a positionable fastening unit and a housing unit with an X-ray source and a collimator unit arranged downstream of the X-ray source arranged on the positionable fastening unit;
displacing collimator plates of the collimator unit for delimiting a collimation field of the collimator unit;
for orienting the collimator unit, controlling the positionable fastening unit to rotate the collimator unit together with the X-ray source while maintaining an orientation of a central beam of the X-ray source, to thereby align the collimation field with an examination region of interest until a match between the examination region of interest and the collimation field is achieved.

8. The method according to claim 7, wherein the positionable fastening unit is movable in a plane.

* * * * *